United States Patent
Pang et al.

(10) Patent No.: US 10,660,596 B2
(45) Date of Patent: May 26, 2020

(54) SELECTING SLICE CONFIGURATION OF MEDICAL IMAGING APPARATUS

(71) Applicant: Beijing Neusoft Medical Equipment Co., Ltd., Beijing (CN)

(72) Inventors: Ling Pang, Shenyang (CN); Shanshan Lou, Shenyang (CN)

(73) Assignee: BEIJING NEUSOFT MEDICAL EQUIPMENT CO., LTD., Beijing (CN)

( * ) Notice: Subject to any disclaimer, the term of this patent is extended or adjusted under 35 U.S.C. 154(b) by 229 days.

(21) Appl. No.: 15/799,586

(22) Filed: Oct. 31, 2017

(65) Prior Publication Data
US 2018/0116619 A1 May 3, 2018

(30) Foreign Application Priority Data
Nov. 1, 2016 (CN) .......................... 2016 1 0942887

(51) Int. Cl.
| A61B 6/00 | (2006.01) |
| A61B 6/03 | (2006.01) |
| A61B 6/02 | (2006.01) |

(52) U.S. Cl.
CPC .............. *A61B 6/488* (2013.01); *A61B 6/027* (2013.01); *A61B 6/032* (2013.01); *A61B 6/542* (2013.01); *A61B 6/545* (2013.01)

(58) Field of Classification Search
None
See application file for complete search history.

(56) References Cited

U.S. PATENT DOCUMENTS

| 5,982,846 A | 11/1999 | Toth et al. |
| 6,141,398 A | 10/2000 | He et al. |
| 6,320,929 B1 | 11/2001 | Von Der Haar |
| 2004/0179644 A1 | 9/2004 | Tsuyuki |
| 2005/0254616 A1 | 11/2005 | Nakanishi et al. |
| 2008/0049889 A1* | 2/2008 | Tsukagoshi ............ A61B 6/032 378/4 |

(Continued)

FOREIGN PATENT DOCUMENTS

| CN | 1895174 A | 1/2007 |
| CN | 102573639 A | 7/2012 |

(Continued)

OTHER PUBLICATIONS

State Intellectual Property Office of the People's Republic of China, Office Action and Search Report Issued in Application No. 201610844028.2, dated Jan. 14, 2019, 9 pages.

(Continued)

*Primary Examiner* — Edwin C Gunberg
(74) *Attorney, Agent, or Firm* — McCoy Russell LLP

(57) ABSTRACT

A method of selecting a slice configuration of a medical imaging apparatus is provided. The method includes: picking out two or more candidate slice configurations from available slice configurations of the medical imaging apparatus; determining a scan dose corresponding to each of the two or more candidate slice configurations; and selecting a candidate slice configuration corresponding to a minimum scan dose as a target slice configuration, where the target slice configuration is used for a current scan protocol.

10 Claims, 3 Drawing Sheets

(56) References Cited

U.S. PATENT DOCUMENTS

2012/0213326 A1* 8/2012 Walker ............... A61B 6/032
378/4
2015/0265226 A1 9/2015 Jackson et al.
2018/0116619 A1 5/2018 Pang et al.

FOREIGN PATENT DOCUMENTS

| CN | 104379059 A | 2/2015 |
| CN | 103494613 B | 10/2015 |
| JP | H11104120 A | 4/1999 |
| JP | 2002102216 A | 4/2002 |
| JP | 2011000134 A | 1/2011 |

OTHER PUBLICATIONS

United States Patent and Trademark Office, Office Action Issued in U.S. Appl. No. 15/711,904, dated Jun. 19, 2019, 32 pages.

* cited by examiner

SELECTING SLICE CONFIGURATION OF MEDICAL IMAGING APPARATUS

CROSS REFERENCE TO RELATED APPLICATIONS

This application claims priority to Chinese Patent Application No. 201610942887.5 entitled "METHOD AND DEVICE FOR SELECTING SLICE CONFIGURATION" filed on Nov. 1, 2016, the entire contents of which are incorporated herein by reference for all purposes.

BACKGROUND

The present disclosure relates to selecting a slice configuration of a medical imaging apparatus.

Computed Tomography (CT) is to perform profile scans one by one for a particular region of a human body by using precisely collimated x-rays and a detector of extremely high sensitivity around the particular region of the human body, thereby obtaining an image of the scanning region for examination of a plurality of diseases.

When a CT apparatus is utilized to perform a spiral scan on a subject, a total scan length may include an effective scan length and a pre-scan length. Where, the effective scan length is a length of a desired scan range selected by a doctor for which a diagnostic image may be produced. The pre-scan length is a part of the total scan length other than the effective scan length and is to be scanned for applying an imaging algorithm. For slice configurations on a CT tube, the wider a selected slice configuration is, the longer a pre-scan length is, resulting in a larger scan dose and a shorter scan time accordingly. On the contrary, the narrower a selected slice configuration is, the shorter a pre-scan length is, resulting in a smaller scan dose and a longer scan time.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

In a spiral scan, a plurality of scan protocols for different scanning regions may be pre-edited, such as a cephalic protocol, an abdominal protocol and a pulmonary protocol, and corresponding slice configurations may be set for different scan protocols. On this basis, when a particular scan protocol is executed, a scan may be performed with a corresponding slice configuration. It may be seen that a scan protocol may correspond to a fixed slice configuration. For a particular scan protocol such as the abdominal protocol, a fixed corresponding slice configuration may lead to a fixed pre-scan length for a subject. With a fixed slice configuration for a scan protocol, a scan dose may be not optimum for a subject. For example, assume a current scan protocol is the abdominal protocol, if a scan dose corresponding to the slice configuration is optimum for an adult, when a subject is a child, the slice configuration may be too wide since an abdominal length of a child is shorter than that of an adult, so that a pre-scan length may be longer than necessary, resulting in an excessive scan dose for a child.

To solve the above problem, a method of selecting a slice configuration is provided according to an example of the present disclosure. According to the method, with scan doses corresponding to candidate slice configurations determined, a minimum dose may be selected from these scan doses, and a slice configuration corresponding to the minimum dose is selected as a target slice configuration to be used for a current scan.

An example of the present disclosure will be specifically described below.

Figure 1:
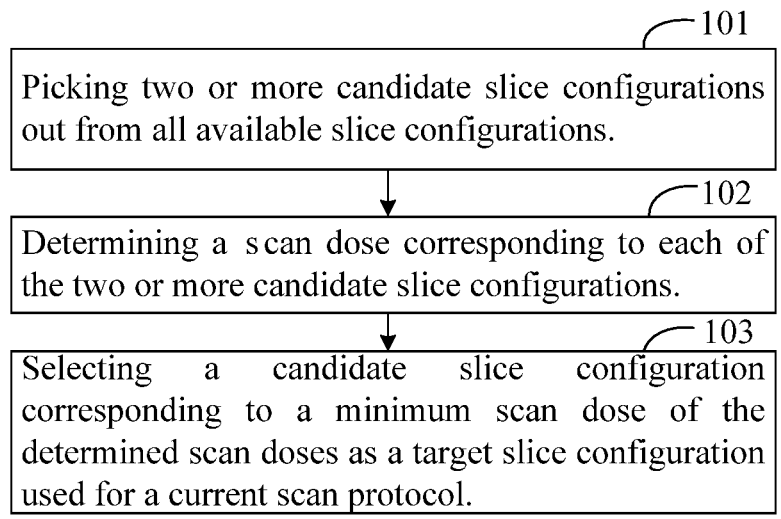
FIG. 1 is a schematic flow diagram of a method of selecting a slice configuration according to an example of the present disclosure.

Referring to FIG. 1, it shows a schematic flow diagram of a method of selecting a slice configuration according to an example of the present disclosure. The method includes blocks 101-103.

At block 101, two or more candidate slice configurations are picked out from all available slice configurations of the medical imaging apparatus.

A slice configuration may be indicated by slice number*slice thickness (usually in mm). Different available slice configurations are provided for different models of CT apparatuses. Taking a 64-row model CT apparatus for example, it may comprise a plurality of available slice configurations such as 64*0.625, 32*0.625, 16*0.625 and 8*0.625. It is to be noted that for a slice configuration, a product of a slice number and a slice thickness is a width of the slice configuration.

In this example, block 101 may be implemented in one of the following two implementations.

In a first implementation, block 101 may include: taking all the available slice configurations as the candidate slice configurations. In such an implementation, if a CT apparatus has N available slice configurations, the N available slice configurations may be selected, where N is an integer and is greater than or equal to 1.

Figure 2:
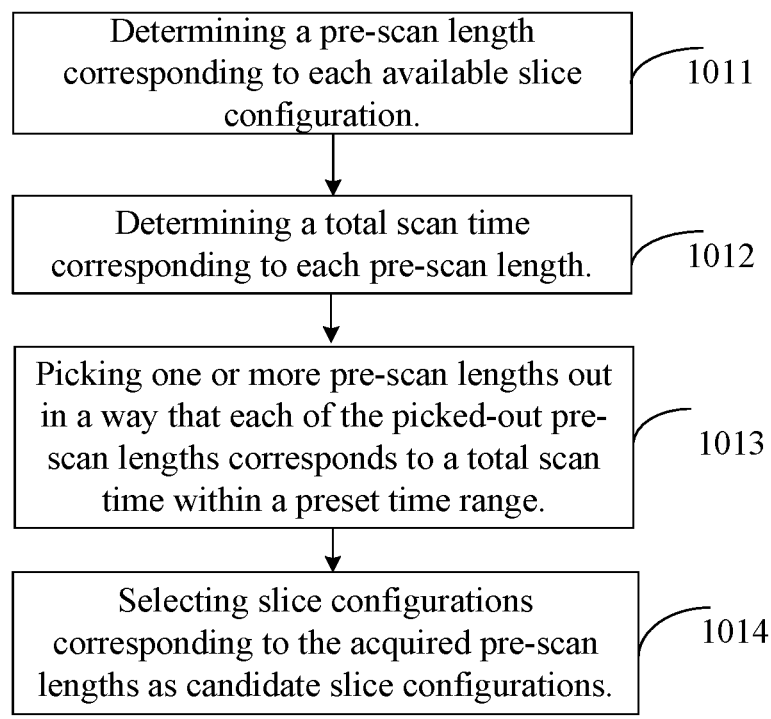
FIG. 2 is a schematic flow diagram of a method of screening slice configurations according to an example of the present disclosure.

In a second implementation, block 101 may include: picking out all or part of the available slice configurations based on respective total scan times corresponding to all the available slice configurations. For example, referring to FIG. 2, which is a schematic flow diagram of a method of screening slice configurations, block 101 may include blocks 1011-1014.

At block 1011, a pre-scan length corresponding to each of the available slice configurations is determined.

In this example, if a CT apparatus has N available slice configurations, corresponding pre-scan lengths may be calculated based on a width of each of the N available slice configurations to acquire N pre-scan lengths, where N is an integer and is greater than or equal to 1.

For example, taking a spiral image reconstruction algorithm Z-Filter for example, a pre-scan length corresponding to a particular slice configuration may be calculated by the following formulas:

$$\text{MaxBeta} = (\text{FilterWeight} + \text{Slice} - 1) * PI / (\text{Slice} * p); \quad (1)$$

$$\text{MinBeta} = -\text{MaxBeta}; \quad (2)$$

$$\text{AnglePerView} = PI * 2 / \text{ViewNumOfCircle}; \quad (3)$$

$$\text{Angle} = (\text{MaxBeta} - \text{MinBeta}) / \text{AnglePerView}; \quad (4)$$

$$\text{ViewRawPreScan} = \text{Angle} * \text{Slice} + 2; \quad (5)$$

where MaxBeta is a maximum sector angle, which is positive; MinBeta is a minimum sector angle, which is negative; FilterWeight is a weighting length of the spiral image reconstruction algorithm Z-Filter; Slice is a width of a particular slice configuration; $PI = \pi = 3.14$; p is a pitch of a spiral scan; AnglePerView is an angle of each view; ViewNumOfCircle is a number of views sampled in a circle of the spiral scan; Angle is a total sector angle; and ViewRawPreScan is a calculated pre-scan length.

Based on each of the above formulas, it may be seen that with other parameters remaining unchanged, the greater a width of a slice configuration, Slice, is, the longer a pre-scan length, ViewRawPreScan, is, and vice versa.

At block 1012, a total scan time corresponding to each of the pre-scan lengths is determined.

A slice configuration may affect a pre-scan length, the pre-scan length may affect a total scan length and the total scan length may affect a total scan time. Therefore, after respective pre-scan lengths corresponding to the N available slice configurations are calculated at block 1011, N total scan times respectively corresponding to the pre-scan lengths may be further calculated. For example, a total scan time desired for scanning with the available slice configuration may be calculated based on a pre-scan length as shown by the following formula (6):

$$\text{Total scan time} = (\text{pre-scan length} + \text{effective scan length}) / (\text{width of slice configuration} * \text{pitch}) \quad (6).$$

At block 1013, one or more pre-scan lengths are picked out in a way that each of the picked-out pre-scan lengths corresponds to a total scan time within a preset time range.

To guarantee a quality of an image reconstructed by a CT apparatus, a total scan time to be taken for scanning a subject generally may not be too long or too short. Therefore, a doctor may preset a time range according to a specific situation of a current scan and his/her experience. It may then be determined whether each of the N total scan times calculated at block 1012 is within the preset time range, thereby picking out M total scan times within the preset time range from the N total scan times, where M<N.

After M total scan times are picked out from the N total scan times, M pre-scan lengths corresponding to the M pieces of total scan time may be acquired.

Figure 3:
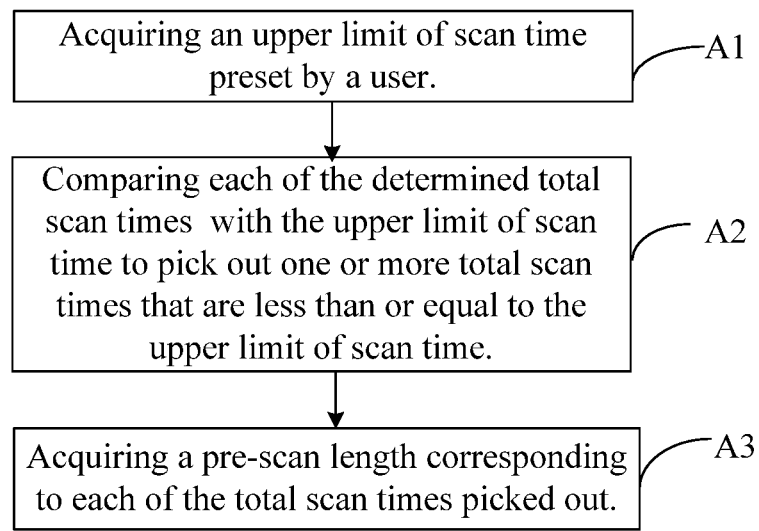
FIG. 3 is a detailed flow diagram of block 1013 in FIG. 2.

In some implementations, as shown in FIG. 3, block 1013 may include blocks A1-A3.

At Block A1, an upper limit of scan time preset by a user may be acquired.

Before performing a scan, an upper limit of scan time may be preset based on a condition of a subject. For example, a patient may usually be requested to hold breath while the lung of the patient is being scanned to avoid a problem of poor image quality due to breathing of the patient. Generally, the shorter a total scan time, the shorter a time span for the patient to hold breath. Therefore, a maximum time span that a patient may be able to hold breath, for example 20 seconds, may be preset as the upper limit of scan time. Thus, a scan to be completed within 20 seconds is acceptable. In another example, when performing a scan of another protocol on a patient, to guarantee a quality of an image reconstructed by a CT apparatus, the patient may be requested to stay still, but a time span that the patient stays still may not be too long. Therefore, a maximum time span that a patient is to stay still, for example 5 minutes, may be preset as the upper limit of scan time. Thus, a scan to be completed within 5 minutes is acceptable.

Based on the above description, block A1 may include: acquiring an upper limit of scan time preset by the user according to the current scan protocol.

Besides, since different patients may have different abilities to hold breath or stay still, a scan that is to be completed within a time span a patient may be able to tolerate is acceptable. Accordingly, block A1 may also include: acquiring an upper limit of scan time preset by the user according to the current scan protocol and endurance of the subject.

At block A2, each of the determined total scan times is compared with the upper limit of scan time, such that one or more total scan times which are less than or equal to the upper limit of scan time may be picked out.

The above calculated N total scan times are compared with the upper limit of scan time, respectively. Each total scan time less than or equal to the upper limit of scan time is picked out from the N total scan times to acquire M total scan times, where M<N.

At block A3, a pre-scan length corresponding to each of the picked out total scan times is acquired.

After M total scan times are picked out, M pre-scan lengths corresponding to the M total scan times picked out are acquired.

At block 1014, slice configurations corresponding to the acquired pre-scan lengths are selected as candidate slice configurations.

Based on M pre-scan lengths acquired at block 1013, M slice configurations corresponding to the M pre-scan lengths may be selected as candidate slice configurations.

At block 102, a scan dose corresponding to each of the candidate slice configurations is determined.

A scan dose of a candidate slice configuration may be determined based on a specification of the slice configuration and other related parameters (e.g., pre-scan length+effective scan length) by using a method of calculating a scan dose known to a person of ordinary skill in the art.

A CT scan on a patient may cause the patient to be exposed to radiation. A degree of the radiation hazard is typically represented by two measurement indexes: Computed Tomographic Dose Index (CTDI) and Dose Length Product (DLP), where the DLP is a parameter related to a total scan length (pre-scan length+effective scan length). The longer the total scan length is, the greater a DLP is, the more radiation caused to the patient is, and vice versa.

For N or M slice configurations picked out at block 101, a scan dose corresponding to each of the candidate slice configurations is calculated. For example, DLP doses may be calculated. Then, different scan doses corresponding to different slice configurations may be determined based on the DLP doses.

At block 103, a candidate slice configuration corresponding to a minimum scan dose of all the determined scan doses is selected as a target slice configuration to be used for a current scan protocol.

For the respective scan doses corresponding to the N or M slice configurations determined at block 102, the slice configuration corresponding to the minimum scan dose may be selected therefrom as the target slice configuration to be used for the current scan protocol.

According to the method of selecting a slice configuration according to the examples of the present disclosure, firstly, two or more candidate slice configurations are picked out from all the available slice configurations. Then, a scan dose corresponding to each of the candidate slice configurations is determined. Finally, the candidate slice configuration corresponding to the minimum scan dose of all the determined scan doses is selected as the target slice configuration to be used for the current scan protocol. It may be seen that with the slice configuration corresponding to the minimum scan dose selected, e.g., a slice configuration having the minimum radiation hazard is selected for the current scan protocol, the problem of a high scan dose when the scan protocol utilizes a fixed slice configuration may be effectively avoided.

The method provided in the present disclosure is described above. An apparatus provided in the present disclosure will be described below.

Figure 4:
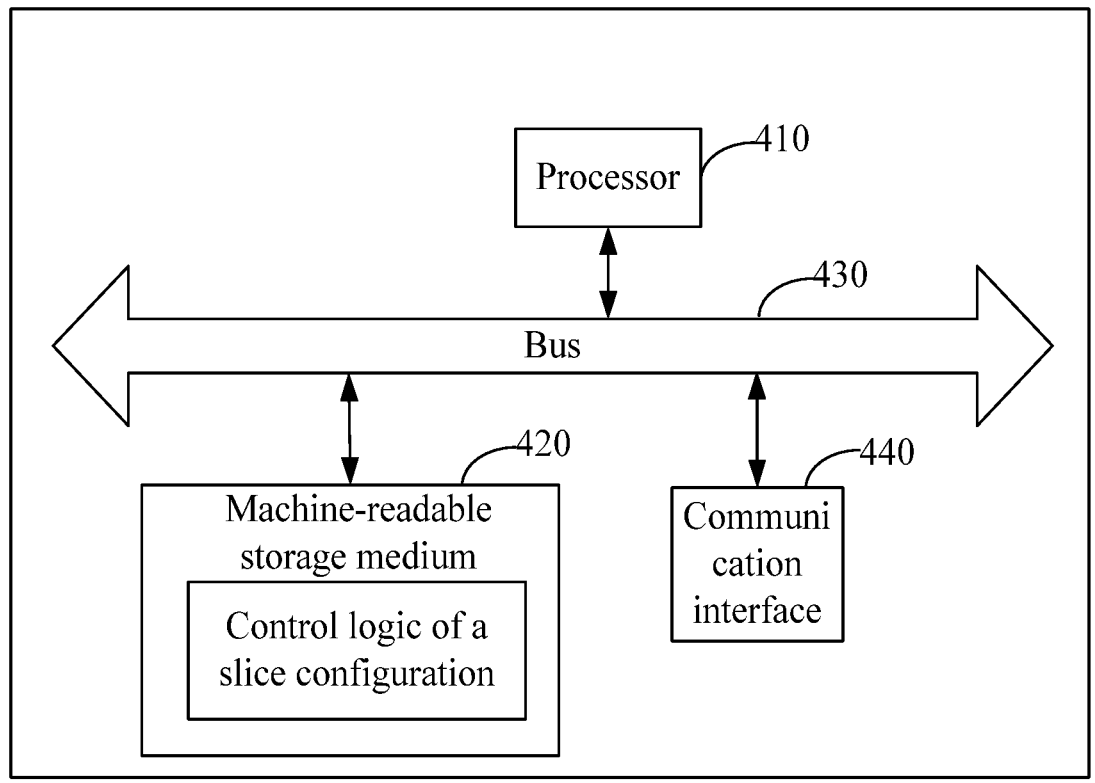
FIG. 4 is a schematic diagram of a hardware structure of a medical imaging apparatus according to an example of the present disclosure.

Referring to FIG. 4, it is a schematic diagram of a hardware structure of a medical imaging apparatus according to an example of the present disclosure. As shown in FIG. 4, the medical imaging apparatus includes a processor 410 and a machine-readable storage medium 420, where the processor 410 and the machine-readable storage medium 420 are typically interconnected by means of an internal bus 430. The medical imaging apparatus may also include a communication interface 440 allowing the apparatus to communicate with other devices or components.

In different examples, the machine-readable storage medium 420 may be: a Read-Only Memory (ROM), a volatile memory, a non-volatile memory, a flash memory, a storage drive (e.g. hard disk drive), a solid state hard disk, any type of storage disk (e.g., optical disk, Digital Video Disk (DVD)), or a similar storage medium, or a combination thereof.

Further, the machine-readable storage medium 420 stores machine-executable instructions corresponding to slice configuration selecting logic. The processor 410 may invoke the instructions of the slice configuration selecting logic stored on the machine-readable storage medium 420 to execute the above-described method of selecting a slice configuration.

The above instructions of the slice configuration selecting logic may be divided into different function modules.

Figure 5:
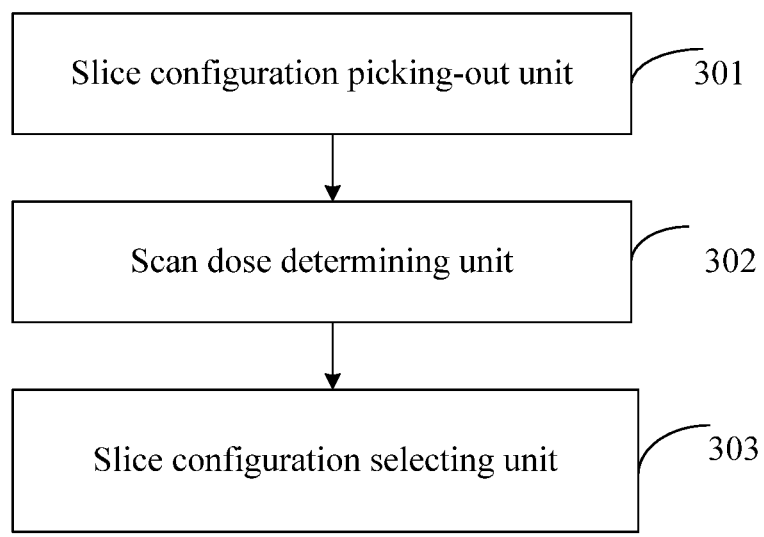
FIG. 5 is a function module block diagram of slice configuration selecting logic according to an example of the present disclosure.

Referring to FIG. 5, it is a function module block diagram of the slice configuration selecting logic according to an example of the present disclosure, including:
a slice configuration picking-out unit 301 configured to pick out two or more candidate slice configurations from all available slice configurations;
a scan dose determining unit 302 configured to determine a scan dose corresponding to each of the two or more candidate slice configurations picked out by the slice configuration picking-out unit 301; and
a slice configuration selecting unit 303 configured to select a candidate slice configuration corresponding to a minimum scan dose of all the scan doses determined by the scan dose determining unit 302 as a target slice configuration to be used for a current scan protocol.

In some implementations, the slice configuration picking-out unit 301 may include a first picking-out unit or a second picking-out unit, where the first picking-out unit is configured to take all the available slice configurations as the candidate slice configurations. The second picking-out unit is configured to pick out all or part of the available slice configurations as the candidate slice configurations based on respective total scan times corresponding to all the available slice configurations.

In some implementations, the second picking-out unit includes a pre-scan length determining subunit, a total scan time determining subunit, a pre-scan length picking-out subunit and a slice configuration selecting subunit, where:
the pre-scan length determining subunit is configured to determine a pre-scan length corresponding to each of the available slice configurations;
the total scan time determining subunit is configured to determine a total scan time corresponding to each of the pre-scan lengths determined by the pre-scan length determining subunit;
the pre-scan length picking-out subunit is configured to pick out one or more pre-scan lengths, so that for each of the acquired pre-scan length, the total scan time determined by the total scan time determining subunit is within a preset time range; and
the slice configuration selecting subunit is configured to select the slice configurations corresponding to the pre-scan lengths acquired by the pre-scan length picking-out subunit as the candidate slice configurations.

In some implementations, the pre-scan length picking-out subunit includes a preset upper limit of scan time acquiring module, a total scan time picking-out module and a pre-scan length acquiring module, where:
the preset upper limit of scan time acquiring module is configured to acquire an upper limit of scan time preset by a user;
the total scan time picking-out module is configured to compare each of the determined total scan times with the preset upper limit of scan time acquired by the preset upper limit of scan time acquiring module, such that one or more total scan times which are less than or equal to the upper limit of scan time may be picked out; and
the pre-scan length acquiring module is configured to acquire a pre-scan length corresponding to each of the total scan times picked out by the total scan time picking-out module.

In some implementations, the upper limit of scan time acquiring module is specifically configured to acquire an upper limit of scan time preset by a user according to a current scan protocol. In some implementations, the upper limit of scan time acquiring module is specifically configured to acquire an upper limit of scan time preset by the user according to a current scan protocol and an endurance of a subject.

In some implementations, the calculation formula for the total scan time is:

$$\text{Total scan time} = (\text{pre-scan length} + \text{effective scan length}) / (\text{width of slice configuration} * \text{pitch}) \quad (6).$$

As used herein, the term "including", "containing" or any variation thereof is intended to encompass non-exclusive inclusion, so that a process, method, article or device including a series of elements includes not only those elements but also other elements not listed explicitly or those elements inherent to such a process, method, article or device. Without more limitations, an element defined by the statement "including a . . . " shall not be precluded to include additional same elements present in a process, method, article or device including the elements.

The above descriptions on the embodiments of the present disclosure enable a person skilled in the art to implement or utilize the present disclosure. Multiple modifications to these embodiments are obvious for those skilled in the art. The general principles defined herein can be implemented in other embodiments without departing from the spirit or scope of the present disclosure. Hence, the present disclosure will not be limited to these embodiments illustrated herein and is intended to conform to the most extensive scope consistent with the principles and novelty characteristics disclosed herein.

The invention claimed is:

1. A method of selecting a slice configuration of a medical imaging apparatus, comprising:
    determining an effective scan length for a to-be-scanned region;
    determining a pre-scan length corresponding to each of a plurality of available slice configurations for the to-be-scanned region; wherein a total scan length for an available slice configuration is a sum of the pre-scan length corresponding to the available slice configuration and the effective scan length;
    for each of the plurality of available slice configurations, determining a total scan time desired for scanning with the available slice configuration based on the total scan length and a width of the available slice configuration;
    picking out two or more candidate slice configurations from the plurality of available slice configurations based on the respective total scan times;
    determining a scan dose corresponding to each of the two or more candidate slice configurations; and
    selecting a candidate slice configuration of the two or more candidate slice configurations corresponding to a minimum scan dose of all the determined scan doses as a target slice configuration, wherein the target slice configuration is used by the medical imaging apparatus for a current scan protocol.

2. The method of claim 1, wherein picking out the two or more candidate slice configurations from the available slice configurations of the medical imaging apparatus comprises:
    taking all the available slice configurations of the medical imaging apparatus as the candidate slice configurations.

3. The method of claim 1, wherein picking out the candidate slice configurations from all the available slice configurations of the medical imaging apparatus based on the respective total scan times comprises:
    selecting one or more slice configurations from all the available slice configurations of the medical imaging apparatus, wherein the total scan time corresponding to each of the selected slice configurations is within a preset time range; and
    taking the selected slice configurations as the candidate slice configurations.

4. The method of claim 3, wherein the preset time range is less than or equal to an upper limit of scan time preset by a user according to the current scan protocol.

5. The method of claim 1, wherein determining the pre-scan length corresponding to the available slice configuration comprises:
    determining a maximum sector angle based on the width of the available slice configuration and a pitch of a spiral scan;
    determining a minimum sector angle based on the maximum sector angle;
    determining a number of views sampled in a circle of the spiral scan;
    determining a total sector angle based on the maximum sector angle, the minimum sector angle and the number of views sampled in the circle; and
    determining the pre-scan length corresponding to the available slice configuration based on the total sector angle and the width of the available slice configuration.

6. A medical imaging apparatus, comprising:
    a processor; and
    a machine-readable storage medium configured to store machine-executable instructions executable by the processor and corresponding to slice configuration selecting logic;
    wherein by executing the machine-executable instructions, the processor is configured to:
    determine an effective scan length for a to-be-scanned region;
    determine a pre-scan length corresponding to each of a plurality of available slice configurations for the to-be-scanned region; wherein a total scan length for the available slice configuration is a sum of the pre-scan length corresponding to the available slice configuration and the effective scan length;
        for each of the plurality of available slice configurations, determine a total scan time desired for scanning with the available slice configuration based on the total scan length and a width of the available slice configuration;
        pick out two or more candidate slice configurations from the plurality of available slice configurations based on the respective total scan times;
        determine a scan dose corresponding to each of the two or more candidate slice configurations; and
        select a candidate slice configuration from the two or more candidate slice configurations corresponding to a minimum scan dose of all the determined scan doses as a target slice configuration, wherein the target slice configuration is used by the medical imaging apparatus for a current scan protocol.

7. The medical imaging apparatus of claim 6, wherein when picking out the two or more candidate slice configurations from the available slice configurations of the medical imaging apparatus, the machine-executable instructions cause the processor to:
    take all the available slice configurations as the candidate slice configurations.

8. The medical imaging apparatus of claim 6, wherein when picking out the candidate slice configurations from all the available slice configurations of the medical apparatus based on the respective total scan times, the machine-executable instructions cause the processor to:
    select one or more slice configurations from all the available slice configurations of the medical imaging apparatus, wherein the total scan time corresponding to each of the selected slice configurations is within a preset time range; and
    take the selected slice configurations as the candidate slice configurations.

9. The medical imaging apparatus of claim 8, wherein the preset time range is less than or equal to an upper limit of scan time preset by a user according to the current scan protocol.

10. A machine-readable storage medium configured to store machine-executable instructions executed by one or more processors, the machine-executable instructions cause the processor(s) to:

determine an effective scan length for a to-be-scanned region;

determine a pre-scan length corresponding to each of a plurality of available slice configurations for the to-be-scanned region; wherein a total scan length for the available slice configuration is a sum of the pre-scan length corresponding to the available slice configuration and the effective scan length;

for each of the plurality of available slice configurations, determine a total scan time desired for scanning with the available slice configuration based on the total scan length and a width of the available slice configuration;

pick out two or more candidate slice configurations from the plurality of available slice configurations based on the respective total scan times, determine a scan dose corresponding to each of the two or more candidate slice configurations; and select a candidate slice configuration from the two or more candidate slice configurations corresponding to a minimum scan dose of all the determined scan doses as a target slice configuration, wherein the target slice configuration is used by the medical imaging apparatus for a current scan protocol.

\* \* \* \* \*